(12) United States Patent
Hassan et al.

(10) Patent No.: US 11,219,780 B2
(45) Date of Patent: Jan. 11, 2022

(54) THERAPEUTIC METHOD AND SYSTEM FOR TREATMENT OF VITAMIN D DEFICIENCY UTILIZING A FULL SPECTRUM OF NATURAL SOLAR RADIATIONS

(71) Applicant: United Arab Emirates University, Al Ain (AE)

(72) Inventors: Ahmed Hassan, Al Ain (AE); Kheira Anissa Tabet Aoul, Al Ain (AE); Rashed Khalifa Al-Shaali, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 17/194,618

(22) Filed: Mar. 8, 2021

(65) Prior Publication Data

US 2021/0187316 A1 Jun. 24, 2021

Related U.S. Application Data

(62) Division of application No. 16/058,457, filed on Aug. 8, 2018, now Pat. No. 10,967,196.

(51) Int. Cl.
*A61N 5/06* (2006.01)

(52) U.S. Cl.
CPC ...... *A61N 5/0613* (2013.01); *A61N 2005/063* (2013.01); *A61N 2005/0626* (2013.01);
(Continued)

(58) Field of Classification Search
CPC .......... A61N 5/0613; A61N 2005/0644; A61N 2005/063; A61N 2005/0667;
(Continued)

(56) References Cited

U.S. PATENT DOCUMENTS

| 4,297,000 A | 10/1981 | Fries |
| 4,306,769 A | 12/1981 | Martinet |

(Continued)

FOREIGN PATENT DOCUMENTS

CN 1548854 A 11/2004

*Primary Examiner* — Eugene T Wu
(74) *Attorney, Agent, or Firm* — Hayes Soloway PC

(57) ABSTRACT

There is provided a therapeutic method and system for utilizing full spectrum of natural solar radiations with an optimum balance of ultra-violet (UV), visible and infrared (IR) radiations. The disclosed therapeutic method comprising collecting and concentrating the natural solar radiations using a natural solar radiations concentrator; transporting the concentrated natural solar radiations using a transporting medium to an indoor device; optimizing a spot size, an intensity and an ultra-violet range of the natural solar radiations; and directing the optimized natural solar radiations to a desired body part using the indoor device; wherein the full spectrum of natural solar radiations has an optimum balance of ultra-violet, visible and infrared radiations. The disclosed therapeutic system comprising an outdoor device for collecting and concentrating the natural solar radiations; and an indoor device in optical communication with the outdoor device for adjusting and directing an optimized amount of the natural solar radiations to a desired body part.

2 Claims, 4 Drawing Sheets

(52) U.S. Cl.
CPC ............... *A61N 2005/0644* (2013.01); *A61N 2005/0657* (2013.01); *A61N 2005/0659* (2013.01); *A61N 2005/0661* (2013.01); *A61N 2005/0662* (2013.01); *A61N 2005/0666* (2013.01); *A61N 2005/0667* (2013.01)

(58) Field of Classification Search
CPC .... A61N 2005/0662; A61N 2005/0666; A61N 2005/0626; A61N 2005/0659; A61N 2005/0657; A61N 2005/0661
See application file for complete search history.

(56) References Cited

U.S. PATENT DOCUMENTS

| | | | |
|---|---|---|---|
| 4,411,490 A * | 10/1983 | Daniel | F21S 11/00 126/648 |
| 4,763,971 A | 8/1988 | Mori | |
| 4,785,811 A * | 11/1988 | Mori | A61N 5/06 607/93 |
| 4,794,925 A * | 1/1989 | Mori | G02F 1/1313 607/93 |
| 4,844,579 A | 7/1989 | Mori | |
| 4,936,668 A * | 6/1990 | Mori | G02B 6/262 385/31 |
| 4,978,186 A | 12/1990 | Mori | |
| 5,575,860 A | 11/1996 | Cherney | |
| 6,129,438 A | 10/2000 | Chubb et al. | |
| 6,603,069 B1 | 8/2003 | Muhs et al. | |
| 7,982,956 B2 | 7/2011 | Kinney et al. | |
| 2004/0054386 A1 | 3/2004 | Martin et al. | |
| 2007/0035841 A1 | 2/2007 | Kinney et al. | |
| 2010/0067114 A1 | 3/2010 | Kinney et al. | |
| 2011/0017199 A1 | 1/2011 | Hernandez et al. | |
| 2013/0144366 A1* | 6/2013 | El-Messeiry | A61N 5/0613 607/93 |
| 2014/0100489 A1 | 4/2014 | Altshuler et al. | |
| 2015/0260431 A1* | 9/2015 | Shenhav | G02B 19/0042 607/88 |

* cited by examiner

THERAPEUTIC METHOD AND SYSTEM FOR TREATMENT OF VITAMIN D DEFICIENCY UTILIZING A FULL SPECTRUM OF NATURAL SOLAR RADIATIONS

CROSS-REFERENCE TO RELATED APPLICATIONS AND PRIORITY

This patent application is a Divisional of U.S. patent application Ser. No. 16/058,457 filed Aug. 8, 2018. This patent application is herein incorporated by reference in its entirety.

FIELD OF THE INVENTION

The present invention relates to the field of utilizing natural solar radiations, and more particularly to a full spectrum of natural solar radiations for prevention or treatment of vitamin D deficiency.

BACKGROUND OF THE INVENTION

Sunlight has been extensively reported as a natural source of generating vitamin D that helps absorb calcium in the body to improve bone health as a direct outcome. Depending on the skin pigmentation, a whole body exposure of 10-60 minutes to sunlight outdoors in the midday without sunscreen can generate up to 10,000 international units (IU) of the vitamin D, being far more than the daily dosage requirement of 400-800 IU reported in various studies. Maintaining vitamin D regulates various functions in the human body that are associated to prevent several diseases including arthritis and cancer. A maintained level of vitamin D is reported to regulate blood pressure, decrease resting heart rate, increase cardiac output, reduce blood cholesterol, increase liver glycogen stores, reduce blood sugar, increase muscular strength and endurance, increase resistance to infections, increase oxygen carrying capacity of blood, increase stress tolerance and increase hormone activity.

Although solar radiation exposure is proven crucial for human health, yet substantial portion of the world population remains deprived of access to the same. The reduced solar exposure fundamentally is driven from two factors i.e. human factor and climatic factor. The human factor includes a number of instances. A busy lifestyle in urban settings that limits outdoor exposure and eventually reduces access to solar radiation. Increased indoor working environments under artificial lighting again deprives occupants from natural sunlight exposure, mobility restriction due to safety concerns in unattended children reduces their outdoor exposure to sunlight, physical conditions in elderly people due to age and illness limits their exposure to natural light and then cultural norms and clothing in certain societies reduces exposure to sunlight specifically in women. Additionally, the perception of skin discoloration discourages general population for outdoor exposure to sunlight in various societies.

The climatic factor is driven by latitude and altitude position of various geographical locations.

The climatic conditions in most of the places being too near or too far from equator are so extreme that it either limits outdoor exposure to sunlight or renders it ineffective. For example, in countries lying between 0-30°, the radiation is so intense with extreme ambient temperature that unprotected outdoor solar exposure for a fairer skin is almost impossible in several months in summer. On the contrary, for countries lying beyond 60° latitude sunlight remains either unavailable or very low for several months in winter that it hardly contains enough ultra-violet (UV) rays required to generate vitamin D On the other hand, exposure to unregulated or intense solar radiation for extended time durations is reported to involve health risks inclusive of sunburn, skin cancer and heat stroke in hot climates.

The increasing amount of ultra-violet (UV) rays in direct sunlight due to ozone depletion strengthens fear of unprotected solar exposure. Eventually, the reduced exposure or overly protected exposure to sunlight triggers a wide spread vitamin D deficiency in the general population leading to more serious health consequences inclusive of rickets, rheumatoid arthritis, cholesterol built up and heart arrest. There is a strong need of providing a safe way to expose to solar radiation eliminating all the risks of over as well as under exposure at the same time respecting the life style demand, protecting physical integrity and addressing cultural concerns.

Safe solar exposure outdoor is increasingly being advocated through sunscreens or sun blockers applied to exposed body parts comprising mainly synthetic chemical compositions. The practice protects from sunburns and associated skin risks but also blocks the useful part of UV radiation responsible for generating vitamin D Additionally, most of the materials employed as sun blockers are toxic thereby polluting the water table and soil through waste water thereby by causing long term environmental sustainability issues. Alternatively, safe access to sunlight indoors has been traditionally practiced through modern architectural designs employing massive glazing as windows, skylight and transition tubes. Increased use of glazing often raises energy efficiency and privacy concerns that in turn is addressed by ensuring code compliance. The energy and privacy code compliance are being achieved by applying spectrally selective coatings on glazing that filter spectral solar radiation often blocking the beneficial part of UV light required to generate vitamin D. The ultimate consequences are recorded in terms of vitamin D deficiency in general masses working indoors for long hours under such even heavily glazed yet so called energy efficient buildings. As a replacement of natural vitamin D reserve achievable through solar exposure, nutrition supplements and fortified foods are extensively being recommended to treat vitamin D deficiency. Although, the supplements and fortification has ironed Vitamin D levels—their comprehensive effects are not well established. In some cases the supplements are reported to produce toxic effects over a longer period of use or else in case of administering excessive dosage.

Sunlight concentration through mirrors and transportation through fibre optics have been demonstrated through several patents. Among the aforementioned, U.S. Pat. No. 5,575,860A exploits only visible part of the solar spectrum to produce electrical energy. U.S. Pat. No. 7,982,956, US20070035841, US20100067114 and U.S. Pat. No. 4,297,000 exploits visible part of solar spectrum to be used as ambient lighting system for visual comfort indoors. CN1548854A exploits thermal part of solar radiations to produce heating systems and U.S. Pat. No. 6,603,069B1 exploits full spectrum sunlight for a hybrid ambient lighting and energy production system. The above mentioned inventions focus solely on energy production and visual comfort without considering physiological needs of human body. Kei Mori's patents (U.S. Pat. Nos. 4,763,971A, 4,844,579A and 4,978,186 A) attempted to utilize solar radiations to illuminate the human body to address its physiological needs. However, it utilizes only the visible part of sunlight overlooking the ultra-violet (UV) and infra-red (IR) parts of which ultra-violet (UV) rays have a crucial role in generating vitamin D and preventing several diseases related to the deficiency condition. Additionally, the inventions have no control over intensity of the incoming radiations that involve the risk of exposure to intense, concentrated radiation leading to heat stroke or skin burns. US20140100489A1 discloses methods of applying radiations from an artificial light source for radiation therapy. The limitation lies in that fact that artificial light cannot compete with natural sunlight to release serotonin (a brain's hormone) believed to improve mood and to render calmness and focus to treat non-seasonal depression, premenstrual dysphoric disorder, and pregnant women with depression. U.S. Pat. No. 6,129,438A discloses whole body exposure to adjustable UVB through artificial lamps to generate vitamin D. US20130144366A1 discloses an ultra-violet (UV) light therapy system through natural sunlight for the treatment of Vitamin D deficiency in a large enclosure, which only transports ultra-violet (UV) light that deprives human body from full spectrum natural light and the benefits of the same thereby involving concerns about health consequences over long terms exposures. Hence, traditional systems deal with transporting visible light which have no role in producing vitamin D, the sunlight exposure is not controlled and has no means of assuring safety, artificial light sources are applied which do not claim the true benefits of natural light and some cases only transport the ultra-violet part which again has no comprehensive effects on human body and the human body remains deprived of the benefits of a full spectrum solar radiation. Another concern is that the exposure of light to body parts is not in line with user preferences and privacy concerns.

The main limitations of traditional systems are that merely the visible part of sunlight is utilized, overlooking the ultra-violet (UV) and infra-red (IR) part of which the ultra-violet (UV) rays have the crucial role in generating vitamin D and preventing several diseases related to a deficiency condition. Additionally, the prior inventions have no control over intensity of the incoming radiations that may certainly involve the risk of exposure to intense, concentrated radiation leading to heat stroke or skin burn. Additionally, traditional systems do not monitor or inform the user of any exposure to the ultra-violet (UV) rays, which has associated risk of lack of vitamin D in case of under exposure and a risk of skin cancer in case of repeated over exposure. Traditional methods for preventing vitamin deficiency are also seen to employ artificial sources of radiations. Such systems are void of several challenges to achieve a desired intensity and spectrum. Further, prior inventions have no control on exposure time and therefore do not indicate safe exposure times or intensity limits to the user and the exposure of radiations to body parts is not in line with user preferences and privacy concerns.

Accordingly, there exists a need to provide a system to utilize a full spectrum of natural solar radiations as prevention or treatment of vitamin D deficiency.

SUMMARY OF THE INVENTION

Therefore it is an object of the present invention to provide a method or system for treatment of vitamin D deficiency utilizing full spectrum of natural solar radiations with an optimum balance of ultra-violet, visible and infrared radiations.

The present invention involves a therapeutic method utilizing a full spectrum of natural solar radiations for prevention or treatment of vitamin D deficiency, wherein the therapeutic method comprises collecting and concentrating the natural solar radiations using a natural solar radiations concentrator, transporting the concentrated natural solar radiations using a transporting medium to an indoor device, optimizing a spot size, an intensity and an ultra-violet range of the natural solar radiations and directing the optimized natural solar radiations to a desired body part using the indoor device, wherein the full spectrum of natural solar radiations has an optimum balance of ultra-violet (UV), visible and infrared (IR) radiations.

In an embodiment, the therapeutic method further comprises collecting and concentrating natural solar radiations through an outdoor device and adjusting and directing an optimized amount of the natural solar radiations through the indoor device.

In another embodiment, the natural solar radiations concentrator is a Fresnel lens, quantum dot concentrator, parabolic trough concentrator or compound parabolic concentrator.

In another embodiment, the indoor device is a handheld device or a fixed device depending on user settings and requirements.

In a preferable embodiment of the present invention. a therapeutic system utilizing a full spectrum of natural solar radiations is disclosed, wherein the therapeutic system comprises an outdoor device for collecting and concentrating the natural solar radiations, and an indoor device in optical communication with the outdoor device for adjusting and directing an optimized amount of the natural solar radiations to a desired body part.

In another embodiment of the present invention, the outdoor device of the therapeutic system further comprises a natural solar radiations concentrator to collect and concentrate natural solar radiations, a receiver and a transporting medium which transports the concentrated natural solar radiations to the indoor device.

In another embodiment of the present invention, the natural solar radiations concentrator is a Fresnel lens, quantum dot concentrator, parabolic trough concentrator or compound parabolic concentrator.

In another embodiment of the present invention, the receiver comprises a tubular hollow core which houses the transporting medium covered with a concentrated photovoltaic cell (CPV).

In another embodiment of the present invention, the transporting medium transports the concentrated natural solar radiations to the indoor device without modifying the full spectrum of natural solar radiations.

In another embodiment of the present invention, an intensity of the concentrated natural solar radiations is controlled by the receiver of the outdoor device.

In another embodiment of the present invention, the transporting medium is an optical fiber bundle, an optical tube or a light pipe.

In another embodiment of the present invention, the concentrated photovoltaic cell (CPV) is positioned on top of the transporting medium to block the concentrated natural solar radiations when the therapeutic system is not in use.

In another embodiment of the present invention, the concentrated photovoltaic cell (CPV) is interfaced with an actuator to lift the concentrated photovoltaic cell, and an electrical connection to feed power produced by the concentrated photovoltaic cell (CPV) to the therapeutic system or store in the battery for later use.

In another embodiment of the present invention, the indoor device is a handheld device.

In another embodiment of the present invention, the indoor device further comprises a display to optimize and display a desired uniform intensity, a diffuser to diverge the concentrated natural solar radiations to generate a uniform radiation spot at the desired body part, a sensor to calculate a time of exposure and the optimum radiation intensity, a butterfly valve which opens or closes to adjust the intensity of the concentrated natural solar radiations, a filter to control an ultra-violet (UV) radiations range and a heat insulation layer to protect the user.

In another embodiment of the present invention, the indoor device is embedded with an algorithm interfaced with the sensor and the actuator to calculate the exposure time of the natural solar radiations based on user-based information.

In another embodiment of the present invention, the user-based information comprises user skin tone, user age, a spot size of natural solar radiations, an intensity of natural solar radiations or an ultra-violet (UV) radiation range of the natural solar radiations.

In another embodiment of the present invention, the indoor device further comprises a switch to turn off the device automatically after a pre-set time of use depending on intensity of the concentrated natural solar radiations.

In another embodiment of the present invention, the indoor device further comprises a device case and a device handle fabricated using a lightweight polycarbonate material.

In another embodiment, the full spectrum of natural solar radiations comprises an optimum balance of ultra-violet (UV), visible and infra-red (IR) radiations.

BRIEF DESCRIPTION OF THE DRAWINGS

The subject matter that is regarded as the invention is particularly pointed out and distinctly claimed in the claims at the conclusion of the specification. The foregoing and other aspects, features, and advantages of the invention are apparent from the following detailed description taken in conjunction with the accompanying drawings in which—

DETAILED DESCRIPTION OF THE INVENTION

Figure 1:
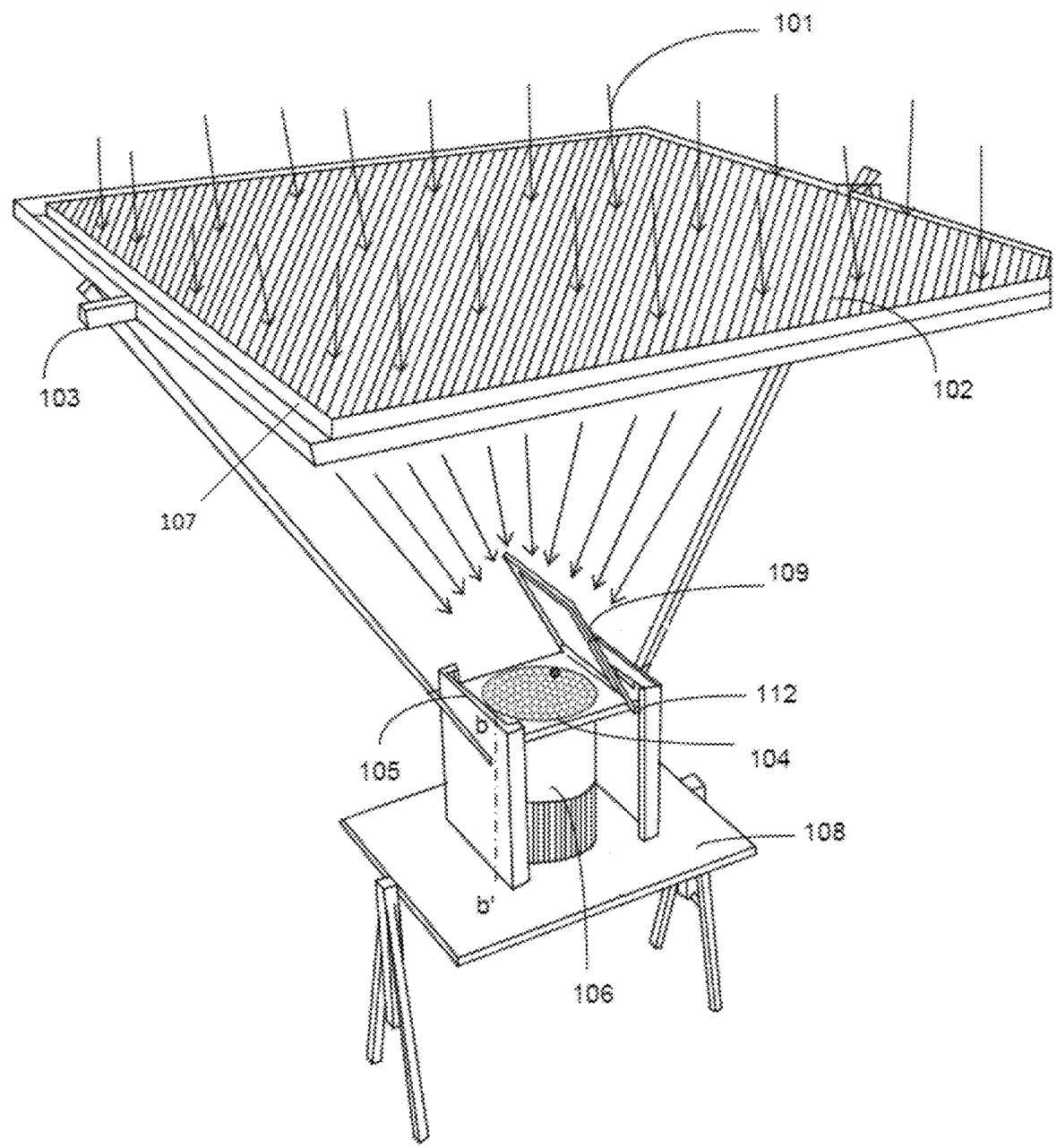
FIG. 1 shows an outdoor device for collecting and concentrating the natural solar radiation.

The aspects of the method or system for treatment of vitamin D deficiency utilizing a full spectrum of natural solar radiations according to the present invention will be described in conjunction with FIGS. 1-3. In the Detailed Description, reference is made to the accompanying figures, which form a part hereof, and in which is shown by way of illustration specific embodiments in which the invention may be practiced. It is to be understood that other embodiments may be utilized and logical changes may be made without departing from the scope of the present invention. The following detailed description, therefore, is not to be taken in a limiting sense, and the scope of the present invention is defined by the appended claims.

The proposed solution aims at providing exposure to full spectrum natural solar radiation instead of filtered ultra-violet (UV) or artificial ultra-violet (UV) radiations, providing radiations at controlled intensity and amount that guarantee risk free exposure eliminating sunburn and skin pigmentation as opposed to uncontrolled outdoor exposure, and customized and movable solar radiation spot exposable at a desired body part to protect sensitive body parts to light like eye retina, avoid glare for light sensitive people and satisfy the cultural preference of preventing discoloration of apparent body parts. The spot size in accordance with the present invention is capable of being tailored as per need and user preferences. The proposed system is also highly applicable in the geographical locations where radiation intensity remains low for several months in winter due to farthest sun position. In winter season of such places, even whole body exposure to sunlight may not generate enough vitamin D to meet body needs.

The problem of low radiation is solved by a concentrator component which increases intensity of both direct and diffused sunlight to levels required for generating substantial amount of vitamin D. On the other hand, the proposed system is equally applicable in the geographical locations where solar radiation stays strong enough in summer months that unprotected outdoor exposure may lead to sunburn or in worst cases heat stroke. In this case, the concentrated sunlight being transported indoors is diffused to achieve a desired intensity and spectrum that guarantees non-burn and risk free expose yet providing solar radiation required to generate vitamin D. More specifically, the approach adopted in our solution resolves barriers of lifestyle, mobility, weather conditions, radiation safety and comfort through an engineered device.

The system in accordance with the present invention comprises mainly of an outdoor device and an indoor device. The outdoor device as shown in FIG. 1 is used for collecting and concentrating the natural solar radiations. The indoor device as depicted in detail in FIG. 3, which is in optical communication with the outdoor device adjusts and directs an optimized amount of the natural solar radiations to a desired body part of a user.

As illustrated in FIG. 1, the outdoor device comprises a sunlight collector or concentrator 102, a receiver 105 to intercept with the concentrated sunlight, a fiber optic cable bundle 104 to transport the concentrated sunlight inside a structure, building or room without modifying the spectrum. In accordance with an embodiment of the present invention, the concentrated solar radiations 101 fall on the receiver 105 which moves up and down in parallel to the beam of concentrated radiations to reach a focal length of desired concentration ratio thereby producing desired radiation intensity. The receiver 105 has a tubular hollow core which houses a bundle of fiber optic cables 104 covered with an operable concentrated photovoltaic cell (CPV) 109 lid. The fiber optic cable bundle 104 consists of combination of carefully selected fibers with a designed mix to achieve a desired spectral range of solar radiations on the transmission side. The optimal combination of the fiber optic types to reclaim the desired spectral range is deemed safe and necessary for generating vitamin D in a human body. The transporting medium or the fiber optic cable bundle 104 transports the concentrated natural solar radiations 101 to an indoor device without modifying the full spectrum of natural solar radiations.

In an embodiment of the present invention, the solar collector or concentrator 102 is arranged on a building skin (roof or facade where applicable).

As shown in FIG. 1, beam of radiations 101 hit the sunlight or solar concentrator 102, which is a Fresnel lens, thereby producing a concentrated beam radiation. Desired concentration of radiations is achieved by refraction through a chain of prisms representing a slope on Fresnel lens surface. The frame of the Fresnel lens 107 comprises a plurality of adjustable nuts 103 to lock the Fresnel lens or solar concentrator 102 in a desired position, to optimize the Fresnel lens or solar concentrator 102 position relative to the incoming solar radiations 101. Intensity of concentrated radiations collected by the bundle of fiber optic cables 104, is controlled by movement of plate of housing 105 up and down in parallel to the incoming solar radiations along the axis denoted as bb'. This movement of the housing plate enables a change in the focus length and thus concentration ratio of the incident radiation beams 101. The natural solar radiations concentrator 102 in accordance with the present invention is a Fresnel lens, quantum dot concentrator, parabolic trough concentrator or compound parabolic concentrator and the transporting medium 104 includes an optical fiber bundle, optical tubes or light pipes.

The fiber optic housing 105 is mechanically coupled by fiber optic coupling and thermally insulated by a fiber protection and insulation layer 106 fixed on a tracking system 108. Movement of fiber optic housing plate of receiver is dictated by the intensity of concentrated natural solar radiations 101 achieved at a user's end. A high temperature concentrated photovoltaic cell (CPV) 109 is placed on top of the bundle of fiber optic cables 104, which is the receiving end of the bundle of fiber optic cables 104 or the transporting medium, in such a way that it can completely block the incoming solar radiations 101 when the indoor device is not intended to provide optimized natural solar radiations to a human body. The concentrated photovoltaic cell (CPV) 109 is interfaced with a mechanical actuator, to lift the photovoltaic cell 109 up as well as with electrical connections to feed power to the therapeutic system. In another embodiment, power is fed into a battery for later use to keep running a display on the indoor device, to optimize and display a desired uniform intensity and for autonomy of use. In an embodiment of the invention, the transporting medium or the bundle of fiber optic cables 104 transports the concentrated natural solar radiations 101 inside a structure or building or room without modifying the spectrum of natural solar radiations 101.

Figure 2:
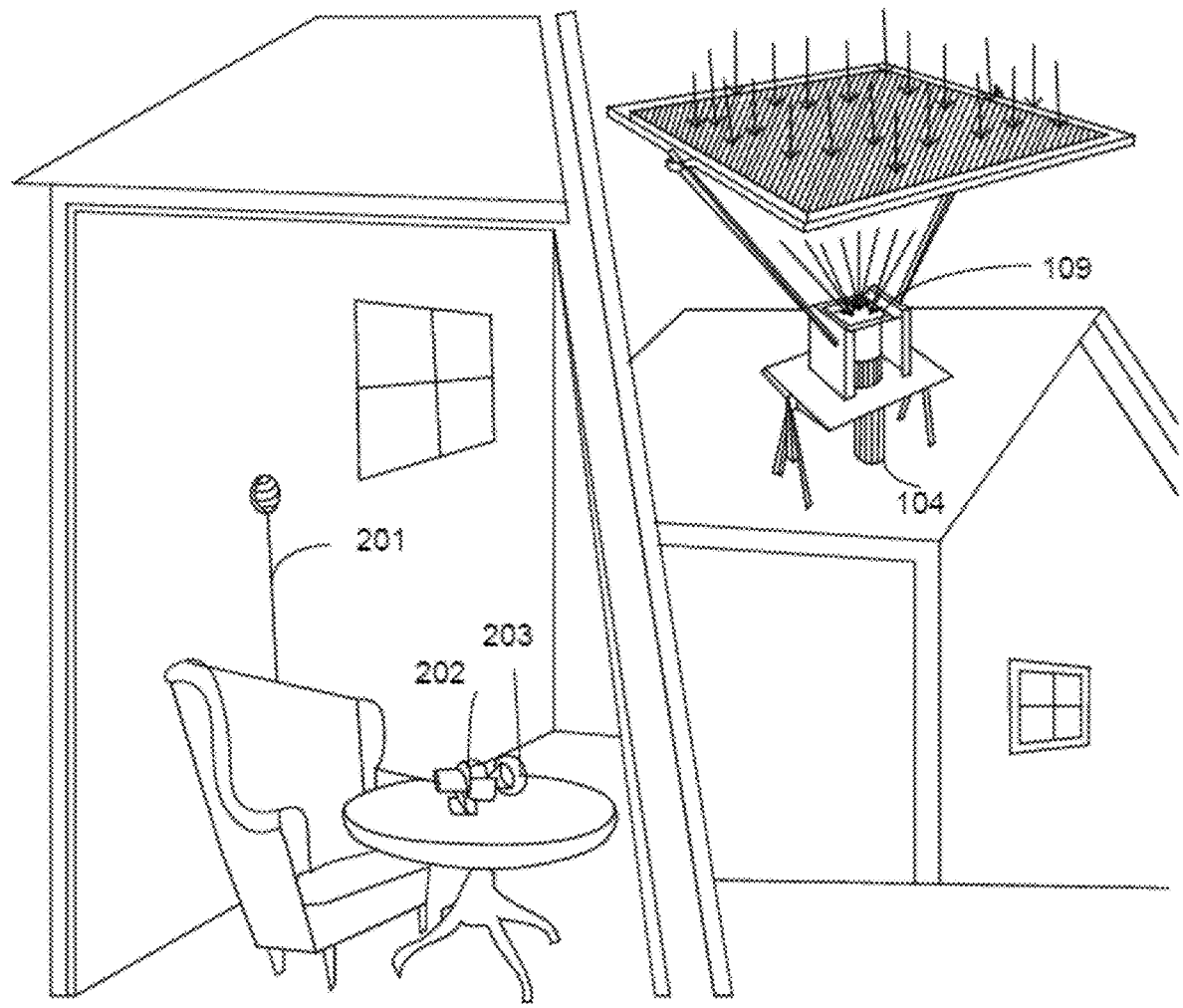
FIG. 2(a) shows a building integration of the therapeutic system with outdoor-indoor device connectivity.
FIG. 2(b) shows an outdoor and indoor device while in use to expose targeted parts of body to the natural solar radiations.
Figure 2:
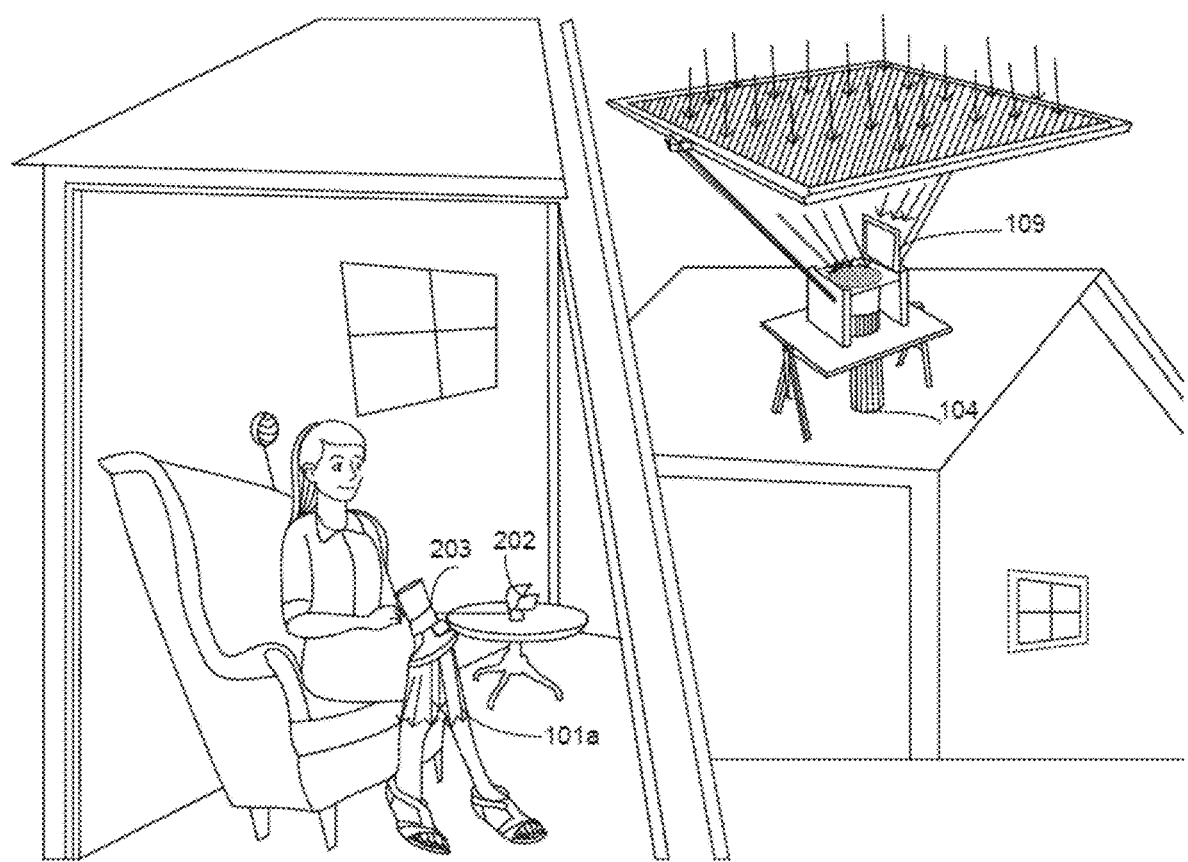

As shown in FIG. 2, the fiber optic bundle 104 is wired into building skin, shown as 201, and thereby transports concentrated radiations to the device 203 placed in device holder 202, which may have various embodiments depending on a setting of use. The possible embodiment of device holder 202 can be public in one case, semi private in another case and private in yet another case represented by a public, office or a home setting. In another embodiment of the present invention, the device 203 can be modified to direct or move a radiation spot. FIG. 2*a* shows a building integration of the therapeutic system with the outdoor-indoor device connectivity and FIG. 2*b* shows the outdoor and indoor device while in use by a user, to expose targeted parts of the body to the natural yet controlled solar radiations 101.

Figure 3:
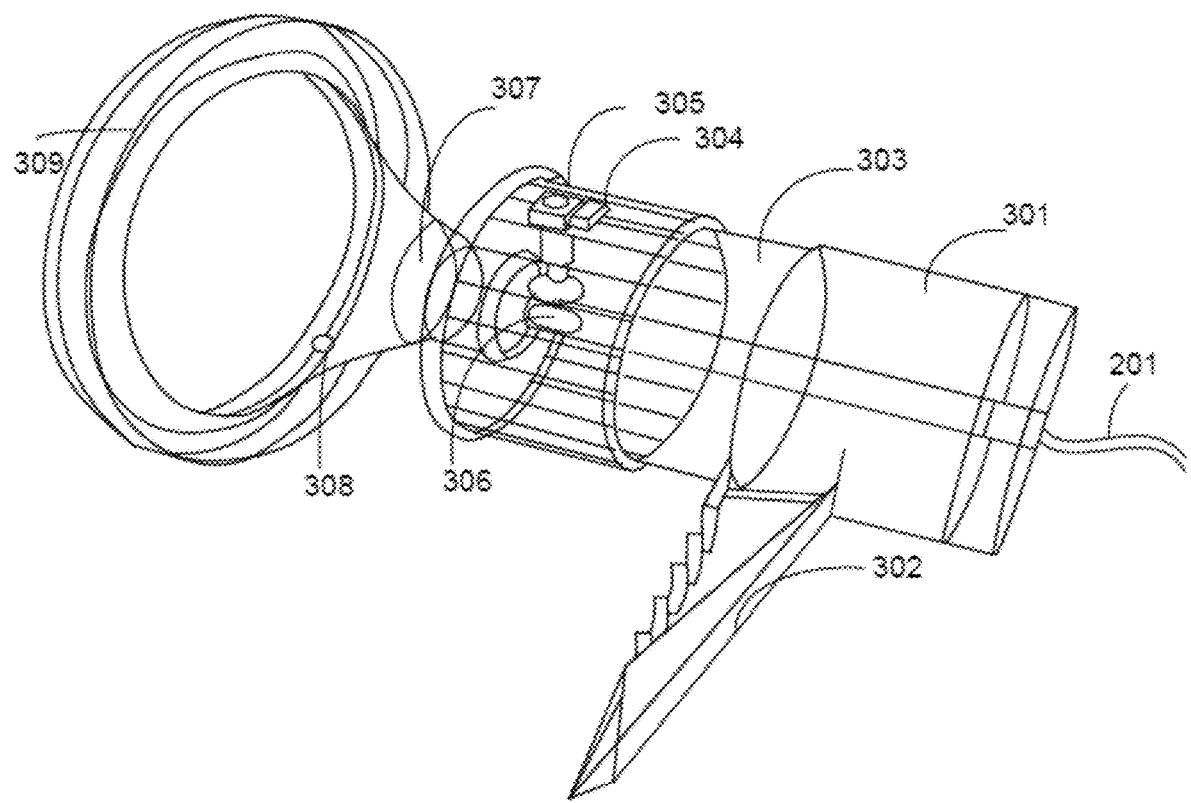
FIG. 3 shows an indoor device for adjusting and directing the optimized amount of the natural solar radiations to the desired body part.

FIG. 3 illustrates an indoor device with detailed components, used for adjusting and directing an optimized amount of the natural solar radiations 101 to a desired body part. Having a robust device case 301 and heat insulation layer 303, the transportation of concentrated radiations is rendered safely in proximity to human body. The diffuser 307 diffuses the concentrated radiations to achieve a comfortable, desired and uniform radiation intensity which is measured by UV index and radiation intensity sensors 308, optimized and displayed on display 304. In case the radiation intensity extends beyond a comfortable range, a butterfly valve 306 opens or closes accordingly to adjust the radiation intensity and to reach a desired value. In case the UV value extends beyond a desired or safe range, the UV filter 309 controls the ultra-violet (UV) range. The indoor device turns off automatically via controller 305 after a pre-set time of use, or when an intensity is reached which is proven by mathematics as acceptable enough to produce a sufficient amount of vitamin D. A sufficient amount of vitamin D depends on age, color, gender and geographical location of a particular user. An automated control of the device 300 eliminates the need for user interference, guarantees ease of use and assures safety. The device case 301 and handle 302 are fabricated using lightweight polycarbonate with a heat insulation layer 303 to ensure that the user is safe from heat.

The concentrated radiation from the outdoor device is thereby fed into a handheld indoor device that monitors the intensity of solar radiations and magnitude of ultra-violet (UV) rays and delivers an optimal amount of the full spectrum of natural solar radiations through a control mechanism. At the exit of the handheld indoor device, a diffuser 307 diverges the concentrated sunlight to generate a uniform radiation spot at desired comfortable intensity to trigger human body. The indoor device is rendered handheld, lightweight and easy to move anywhere in proximity to the desired part of the body with the desired spot size. The indoor device is embedded with an algorithm interfaced with sensors and actuators to calculate time of exposure for a user based of user's skin tone, user's age, incident solar radiation spot size, incident solar radiation intensity and incident solar radiation UV index, and hence adjusts and directs an optimized and suitable amount of the natural solar radiations to a desired body part.

In an embodiment of the present invention, the indoor device is a handheld device or a fixed device depending on user settings and requirements. The indoor device is capable of being picked up and used by a user to direct radiations to a required or desired area whereas, in another scenario, the indoor device is also capable of being fixed on a fixture while the radiation spot is movable for illuminating various desired body parts or areas.

The indoor device as shown in FIG. 3 features safety functioning in terms of solar radiation intensity and the UV index. The indoor device will automatically close through actuators that will deactivate emission of solar radiation if any of safety concerns are recorded. The indoor device is installable in multiple building types and occupancy patterns including homes, schools, offices and hospitals to cure or prevent vitamin D deficiency while at work or leisure being handheld or fixed in place or both.

In an embodiment of the present invention, the transporting medium 104 consists of combination of carefully selected optical fibers with a designed mix to achieve a desired spectral range of natural solar radiations on the transmission side. The optimal combination of the optical fiber types to reclaim the desired spectral range deemed safe and necessary for generating vitamin D in the human body is an important feature of the present invention.

The therapeutic system in accordance with the present invention utilizing full spectrum of natural solar radiations with an optimum balance of ultra-violet, visible and infrared radiations features an important safety function in terms of natural solar radiation intensity and the ultra-violet (UV) range. The therapeutic system automatically stops by closing the concentrated photovoltaic cell (CPV) 109 through an actuator which blinds the optical fiber bundle 104 of natural solar radiations 101 if any of the safety concerns are recorded by the tracking system 108.

In a preferred embodiment of the present invention, a full spectrum of natural solar radiations 101 containing right balance of ultra-violet, visible and infrared (IR) is achieved through this proposed system. This is achieved by designing the fiber optic bundle 104 to have an appropriate core to cladding diameter ratios. Yet another advantage of the proposed system is maintaining an optimum solar radiation intensity that guarantees non-burn conditions through sustaining an optimal distance between the natural solar radiations concentrator 102 to the receiver 105 depending on respective geographical locations. Further, it is possible to direct the optimized natural solar radiations to a desired body part via the portable and light-weight indoor device 203 and thus achieve controllable spot sizes—with respect and consideration to a user's privacy and preference.

In another embodiment of the present invention, the spot size is tailored in accordance with a user's need and preference, ranging from a few centimeters to whole body exposure in another embodiment. A possible implementation the indoor device in accordance with the present invention is public in one case, semi private in another case and private in yet another case represented by a public, office or home setting.

In another preferred embodiment of the present invention, the therapeutic system in accordance with the present invention is used to cure or prevent vitamin D deficiency. In another embodiment, the therapeutic system is used to improve mood and work focus.

The present invention transports full spectrum sunlight and thus brings the associated comprehensive health benefits compared to transport of visible sunlight and ultra-violet (UV) part only. The proposed solution employs a natural means of generating vitamin D, by exploiting UVB in natural sunlight through a device compared to employing and artificial device producing UV, guaranteeing an optimal combination of UV, Visible, and IR radiations intended to produce comprehensive health effects on human body by designing optimum combination of various core fiber optic bundle characterized by core to cladding diameter ratios. Through such a treatment, the range of the transmitted wavelength can be controlled to achieve desired solar spectrum that is believed to be safe and effective for human health. Consequently, the device can handle variation of UV index in different climatic zone and at different times of day which is extremely advantageous compared to uncontrolled radiation hitting human body, incomplete solar spectrum limited to UV only and artificial UV.

The present solution adjusts intensity of solar radiations hitting the human body by incorporating a radiation monitoring sensor 308 at the outlet of the diffuser 307 feeding back to a controller thereby actuating movement of the receiver 105 up or down along bb' until the desired intensity is achieved. These measures assure radiation safety even at different times of the day, different climates, different seasons of the year and the need of the human body as per ethnicity, age and gender compared to uncontrolled exposures which do not address any of the stated concerns. The proposed system assures safety by closing off automatically if safety concerns are not resolved, and further allows freedom of exposure to a preferred part of the body, in contrast to a whole body exposure, thus addressing several social and cultural concerns of privacy and sensitivity to skin discoloration.

The handheld indoor device enables preferential body part exposure in order to protect sensitive body parts in case of the ailment or sensitivity such as autism, ensuring safe time durations of exposure to solar radiation to produce right amount of vitamin D for people of different age, gender and ethnicity by measuring the radiation intensity, UV index and spot size of the radiation on the exposed body. The measured values used by an algorithm to determine net time duration of exposure per session or over several sessions as per requirement and history. The measurement and calculation methods in the present invention is reliable, being based on a measured value of the UV index, solar radiation intensity and spot size. Any device intended to monitor vitamin D must be based on measured UV rather than visible for precise determination to avoid the risks involved due to over exposure to UV that may cause skin burn.

Many changes, modifications, variations and other uses and applications of the subject invention will become apparent to those skilled in the art after considering this specification and the accompanying drawings, which disclose the preferred embodiments thereof. All such changes, modifications, variations and other uses and applications, which do not depart from the spirit and scope of the invention, are deemed to be covered by the invention, which is to be limited only by the claims which follow.

The invention claimed is:

1. A therapeutic method utilizing a full spectrum of natural solar radiations for prevention or treatment of vitamin D deficiency, wherein the method comprises:
    collecting and concentrating the natural solar radiations using an outdoor device;
    transporting the concentrated natural solar radiations using a transporting medium to an indoor device;
    optimizing a spot size, an intensity and an ultra-violet range of the natural solar radiations; and
    directing the optimized natural solar radiations to a desired body part using the indoor device,
    wherein the indoor device is a handheld device, and
    wherein the outdoor device further comprises:
        a natural solar radiations concentrator to collect and concentrate natural solar radiations;
        a receiver; and
        the transporting medium that transports the concentrated natural solar radiations to the indoor device, and
        wherein the transporting medium transports the concentrated natural solar radiations to the indoor device without modifying the full spectrum of natural solar radiations.

2. The therapeutic method of claim 1, wherein the natural solar radiations concentrator is a Fresnel lens, quantum dot concentrator, parabolic trough concentrator or compound parabolic concentrator.

* * * * *